United States Patent
Sekino et al.

(10) Patent No.: US 6,187,701 B1
(45) Date of Patent: Feb. 13, 2001

(54) DENTAL PORCELAIN

(75) Inventors: Masato Sekino, Tsukuba; Hiroyuki Nakagawa, Shimotsuma; Osamu Iwamoto, Tsukuba; Masaaki Ushioda, Shimodate, all of (JP)

(73) Assignee: Tokuyama Corporation, Yamaguchi-ken (JP)

( * ) Notice: Under 35 U.S.C. 154(b), the term of this patent shall be extended for 0 days.

(21) Appl. No.: 09/321,551

(22) Filed: May 28, 1999

(30) Foreign Application Priority Data

May 29, 1998 (JP) .................................................. 10-149402

(51) Int. Cl.[7] .............................. C03B 8/04; C03B 3/093; A61C 13/083
(52) U.S. Cl. ................................ 501/67; 501/17; 501/21; 501/66; 501/68; 501/69; 106/35
(58) Field of Search .................................. 501/66, 67, 68, 501/69, 17, 21; 106/35

(56) References Cited

U.S. PATENT DOCUMENTS 4,120,729 * 10/1978 Smyth et al. ........................... 106/35
5,304,516 * 4/1994 Clifford .................................. 501/66
5,614,330 * 3/1997 Panzera et al. ........................ 501/21

* cited by examiner

Primary Examiner—C. Melissa Koslow
(74) Attorney, Agent, or Firm—Wenderoth, Lind & Ponack, L.L.P.

(57) ABSTRACT

Provided is a porcelain which is suitable as a dental porcelain capable of being fired on a ceramics core and has a low firing temperature and a low thermal expansion coefficient and which is excellent in a chemical durability. The above dental porcelain comprises glass containing silicon oxide, aluminum oxide, boron oxide, zinc oxide, sodium oxide and lithium oxide as principal components. The contents of these respective components in the above glass are 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$ respectively in terms of a percent by weight based on the total of the respective components when the respective components are reduced to $SiO_2$, $Al_2O_3$, $B_2O_3$, ZnO, $Na_2O$ and $Li_2O$ respectively. The particularly preferred dental porcelain comprises glass having a thermal expansion coefficient of $6.0 \times 10^{-6}$ (1/°C.) or less as a principal structural component.

16 Claims, 1 Drawing Sheet

DENTAL PORCELAIN

The present invention relates to a dental porcelain. More specifically, the present invention relates to a dental porcelain capable of being used for a ceramics core having a low thermal expansion coefficient.

In odontotherapy, especially for aesthetic tooth restorations, dental prostheses, such as an artificial tooth, inlays, onlays, bridges and crowns, which use dental porcelains have been used. There are two types of dental prostheses. One type is a metal-reinforced dental prosthesis which is produced by firing a porcelain called a metal bond porcelain on a metal core; the other type is a full ceramics (synonymous with all ceramics) dental prosthesis which is produced by firing a porcelain on a ceramic core.

The metal-reinforced dental prosthesis has been widely used because it has a high strength. Further, ceramics which contain crystalline components, e.g. orthoclase ($KAlSi_3O_8$), albite ($NaAlSi_3O_8$) and the like are widely used as metal bond porcelains. However, two serious problems are caused when they are used. That is, one problem is that gum discolors due to elution of metal ions, and the other is that the metal in the inside (metal core) shuts off light and therefore natural translucent feeling can not be obtained.

In contrast with this, when the full ceramics dental prostheses are used, such serious problems shall not take place. Then, in the field of dental prostheses, especially in the field of dental porcelain crowns where aesthetic aspect is very important new ceramic materials having an excellent strength have been developed, and therefore the importance of the full ceramics prostheses has been increasing.

In general, a dental porcelain crown is produced by using porcelains having color tones which correspond to those of the respective parts of the crown for the respective parts thereof in order to obtain appearance close to that of a natural tooth.

BRIEF DESCRIPTION OF DRAWING

The attached drawing is a cross section showing an example of such crown. To be specific, as shown in FIG. 1, the above crown is produced by firing a body porcelain 4 (synonymous with a body dentin porcelain) for reproducing an ivory color, a cervical porcelain (synonymous with gingival dentin porcelain) for reproducing a cervial color, an incisal porcelain 3 (synonymous with an enamel porcelain) for reproducing an incisal color and a translucent porcelain 2 for displaying a translucent feeling respectively in a layer form on a core 1 fitted to an abutment tooth 6.

In general, these various porcelains are prepared by blending powder ceramic components having an average particle diameter of 15 to 100 $\mu$m with pigments having compositions corresponding to the respective porcelains.

Figure 1:
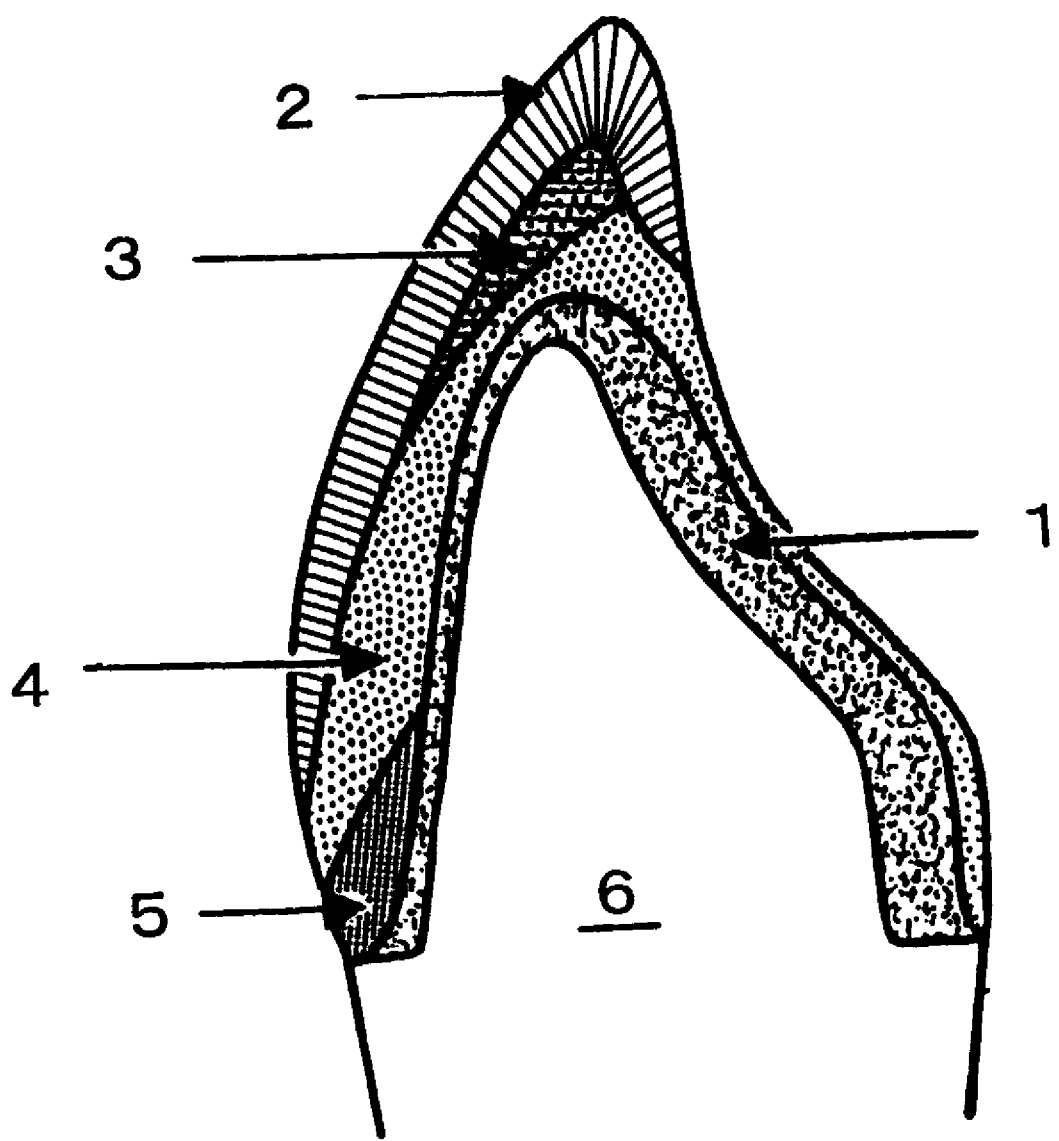

It is difficult to reproduce a delicate color tone of a natural tooth and patters intrinsic to individuals only by laminating and firing the respective porcelains described above, and therefore a porcelain containing a relatively large amount of a pigment called stain powders (synonymous with effective powders) is used to provide coloring, or a porcelain called glaze powders and scarcely containing a pigment is fired to smoothen the surface or provide translucence. In general, an average particle diameter of the ceramics components in the stain powder and glaze powders described above is set to 1 to 15 $\mu$m which is smaller than those of the foregoing body porcelain and the like in order to reproduce a delicate color and a surface texture.

In a dental porcelain crown, it is important for preventing peeling of the porcelain and production of cracks due to stress originating in a difference in a contraction between the core material and the porcelain caused in cooling down after firing in the production thereof that the thermal expansion coefficients of the porcelains and the core ceramics are close to each other. There have so far been used for core ceramics, glass ceramics having usually a thermal expansion coefficient of $7 \times 10^{31\ 6}$ to $13 \times 10^{-6}/°$ C. such as mica, apatite and calcium phosphate. However, a diopside base core material which has newly been developed in recent years as a core ceramics material having a good press moldability has as low thermal expansion coefficient as 4 to $6 \times 10^{-6}$ (1/° C.), and porcelains which can be fired on such ceramics core as having a low thermal expansion coefficient have not yet been developed.

Further, when a porcelain is fired on a ceramics core of a glass ceramics base, the porcelain has to be fired at a temperature of not higher than a distortion point of the ceramics core in order to prevent a deformation of the core and production of heat distortion thereof in forming. Further, the porcelain is used on sever conditions in the buccal cavity over an extended period or time, and therefore a chemical durability such as a dissolution resistance against, for example, an acid solution is requested.

An object of the present invention is to provide a dental porcelain which is suitable as a porcelain capable of being fired on a ceramics core having such low thermal expansion coefficient as described above and has a low required firing temperature and a low thermal expansion coefficient and which is excellent in a chemical durability.

The present inventors have repeated intensive researches in order to overcome the technical problems described above. As a result thereof, they have found that a dental porcelain which has a low firing temperature and a low thermal expansion coefficient and which is excellent in a chemical durability can be obtained by using glass having a specific composition, and they have come to complete the present invention.

Thus, according to the present invention, provided is a dental porcelain comprising glass containing silicon oxide, aluminum oxide, boron oxide, zinc oxide, sodium oxide and lithium oxide as principal components, wherein the contents of these respective components in the above glass are 57 to 65% by weight of $SiO_2$, 8 to 18% by weight of $Al_2O_3$, 15 to 25% by weight of $B_2O_3$, 0.1 to 2% by weight of $ZnO$, 3 to 7% by weight of $Na_2O$ and 2 to 8% by weight of $Li_2O$ respectively in terms of a percent by weight based on the total of the respective components when the respective components are reduced to $SiO_2$, $Al_2O_3$, $B_2O_3$, $ZnO$, $Na_2O$ and $Li_2O$ respectively.

Among the dental porcelains described above, those having a thermal expansion coefficient of $6.0 \times 10^{-6}$ (1/° C.) or less can suitably be applied to a ceramics core having a low thermal expansion coefficient such as a diopside base ceramics core.

Further, according to the present invention, provided is a glass containing silicon oxide, aluminum oxide, boron oxide, zinc oxide, sodium oxide and lithium oxide as principal components, wherein the contents of these respective components are 57 to 65% by weight of $SiO_2$, 8 to 18% by weight of $Al_2O_3$, 15 to 25% by weight of $B_2O_3$, 0.1 to 2% by weight of $ZnO$, 3 to 7% by weight of $Na_2O$ and 2 to 8% by weight of $Li_2O$ respectively in terms of a percent by weight based on the total of the respective components when the respective components are reduced to $SiO_2$, $Al_2O_3$, $B_2O_3$, $ZnO$, $Na_2O$ and $Li_2O$ respectively; and the thermal expansion coefficient thereof is $6.0 \times 10^{-6}$ (1/°C.) or less.

The above glass can suitably be used as a raw material for the foregoing dental porcelain of the present invention.

The dental porcelain of the present invention comprise mainly the glass containing the specific component described above in a specific proportion (that is, a specific composition). In this case, a dental porcelain means porcelains used for producing dental prostheses such as artificial tooth, inlay, onlay, bridge and crown, that is, porcelains which are laminated on ceramics cores and metal cores. However, it is most effective to use the dental porcelain of this invention for cores having low thermal expansion coefficients, so that the porcelain described above can be used preferably for making full ceramics crowns.

The glass having the specific composition described above which constitutes the dental porcelain of the present invention contains silicon oxide, aluminum oxide, boron oxide, zinc oxide, sodium oxide and lithium oxide as principal components, and the contents of these respective components fall in the following ranges respectively in terms of a percent by weight based on the total weight (hereinafter referred to as a standard weight) of the respective components when the respective components are reduced to $SiO_2$, $Al_2O_3$, $B_2O_3$, $ZnO$, $Na_2O$ and $Li_2O$ respectively. In the present specification, the contents of the respective components in the glass described above shall hereinafter be meant by the foregoing percents by weight.

That is, the content of silicon oxide in the glass described above is 57 to 65% by weight, preferably 57 to 62% by weight. If the content of silicon oxide exceeds 65% by weight, the melting temperature for preparing the glass grows too high, and even if the glass could be prepared at a high temperature, the firing temperature of the glass shall be elevated. On the other hand, if the content is less than 57% by weight, the chemical durability is reduced when used as a dental porcelain.

Also, the content of aluminum oxide in the glass described above is 8 to 18% by weight, preferably 10 to 15% by weight. If the content of aluminum oxide exceeds 18% by weight, the viscosity of the glass at a high temperature grows large, and therefore the firing temperature is elevated. On the other hand, if the content is less than 8% by weight, the chemical durability is reduced when used as a dental porcelain.

Further, the content of boron oxide in the glass described above is 15 to 25% by weight, preferably 15 to 20% by weight. If the content of boron oxide exceeds 25% by weight, the chemical durability is reduced when used as a dental porcelain. On the other hand, if the content is less than 15% by weight, the firing temperature thereof is elevated.

The content of zinc oxide in the glass described above is 0.1 to 2% by weight, preferably 1 to 2% by weight. Zinc oxide acts as a fusing agent in the glass described above. If the content thereof exceeds 2% by weight, the chemical durability is reduced, and if it is less than 0.1% by weight, an effect as the fusing agent is not shown.

The content of sodium oxide in the glass described above is 3 to 7% by weight. Sodium oxide acts as a fusing agent in the glass described above. If the content thereof exceeds 7% by weight, the thermal expansion coefficient grows large, and peeling is caused when it is fired on a ceramics core. At the same time, the chemical durability is reduced. On the other hand, if the content of sodium oxide is less than 3% by weight, the melting temperature for preparing the glass grows too high, and even if the glass could be prepared at a high temperature, the firing temperature of the glass shall be elevated.

Further, the content of lithium oxide in the glass described above is 2 to 8% by weight. The content of lithium oxide is preferably 3 to 8% by weight for controlling the thermal expansion coefficient of the glass to a lower level and reducing the required firing temperature to, for example, 750° C. or lower.

When the glass described above comprises only the respective essential components described above, it shows as well a satisfactory effect when it is used as a dental porcelain, and a reduction in the firing temperature and a decrease in bubbles in the fired article can be achieved by further adding at lest one oxide selected from the group consisting of calcium oxide, magnesium oxide and barium oxide in addition to the essential components described above. The effect described above grows high when the blending amount of these oxides is 5% by weight or less based on a weight obtained by adding the weights of these oxides to the standard weight when these oxides are reduced to CaO, MgO and BaO, and it is particularly preferred.

Thus, the glass capable of being used for producing the dental porcelain of the present invention contains silicon oxide, aluminum oxide, boron oxide, zinc oxide, sodium oxide and lithium oxide as principal components, wherein the contents of these respective components are 57 to 65% by weight of $SiO_2$, 8 to 18% by weight of $Al_2O_3$, 15 to 25% by weight of $B_2O_3$, 0.1 to 2% by weight of $ZnO$, 3 to 7% by weight of $Na_2O$ and 2 to 8% by weight of $Li_2O$ respectively in terms of a percent by weight based on the total of the respective components when the respective components are reduced to $SiO_2$, $Al_2O_3$, $B_2O_3$, $ZnO$, $Na_2O$ and $Li_2O$ respectively; at lest one oxide selected from the group consisting of calcium oxide, magnesium oxide and barium oxide is contained in a proportion of 0.1 to 5% by weight based on a weight obtained by adding the weights of these oxides to the standard weight when these oxides are reduced to CaO, MgO and BaO; and the thermal expansion coefficient thereof is $6.0 \times 10^{-6}$ (1/°C.) or less.

Further, the glass described above can be blended with various metal oxides in addition to the essential components described above as long as an adverse effect is not exerted on the effects of the present invention. Examples of these metal oxides include transition metal oxides such as vanadium oxide, chromium oxide, manganese oxide, iron oxide, cobalt oxide, nickel oxide, copper oxide and zirconium oxide; lanthanoid oxides such as lanthanum oxide, yttrium oxide and tantalum oxide; and in addition thereto, strontium oxide, phosphorus oxide and tin oxide.

The glass described above may be produced by any method and can be produced, for example, by blending first raw materials for the respective essential components described above and, if necessary, raw materials for the optional components described above in the prescribed amounts respectively and melting the resulting mixture, followed by cooling it down.

The raw materials for the respective components described above shall not specifically be restricted as long as they are the respective components themselves and/or materials which are turned into the respective components when heated in the presence of oxygen. Examples of the materials capable of being suitably used for the raw materials for the glass of the present invention shall specifically be given below.

In general, silica sand ($SiO_2$) is used as a raw material for silicon oxide.

A raw material for aluminum oxide includes alumina ($Al_2O_3$) and aluminum hydroxide [$Al(OH)_3$].

A raw material for boron oxide includes boric anhydride ($B_2O_3$) and anhydrous silica sand ($Na_2B_4O_7$).

Zinc oxide (ZnO) is mainly used as a raw material for zinc oxide.

Soda ash ($Na_2CO_3$), sodium hydroxide (NaOH), sodium sulfate ($Na_2SO_4$) and sodium nitrate ($NaNO_3$) can be used as a raw material for sodium oxide.

Lithium carbonate ($Li_2CO_3$), lithium hydroxide (LiOH), lithium sulfate ($Li_2SO_4$) and lithium nitrate ($LiNO_3$) can be used as a raw material for lithium oxide.

Calcium carbonate ($CaCO_3$), calcium hydroxide [$Ca(OH)_2$], calcium sulfate ($CaSO_4$) and calcium nitrate [$Ca(NO_3)_2$] can be used as a raw material for calcium oxide.

Magnesium carbonate ($MgCO_3$) or magnesium hydroxide [$Mg(OH)_2$] is usually used as a raw material for magnesium oxide, and magnesium sulfate ($MgSO_4$) and magnesium nitrate [$Mg(NO_3)_2$] may be added for the purpose of a clarifying action.

The raw materials described above may be used alone or in a mixture of plural kinds of the respective components.

The raw materials described above are mixed after determining the use amounts thereof in advance by calculation taking the composition of the glass finally obtained into consideration. The mixing method shall not specifically be restricted as long as it is a method by which the respective raw materials can homogeneously be dispersed, and it can be carried out by means of publicly known mixers such as a V type mixer, a ball mill and the like. The melting method of the mixture described above shall not specifically be restricted, and the mixture can be charged into a crucible and molten by heating in an electric furnace. The melting conditions shall not specifically be restricted as long as the whole mixture of the raw materials is molten and the components are not sublimated. In general, the mixture can be heated at 1300° C. The cooling conditions after melting shall not specifically be restricted as well, and cooling can be carried out by cooling slowly in the air or quenching in water.

The glass thus obtained has usually as low thermal expansion coefficient as $6.0 \times 10^{-6}$ (1/°C.) or less (that is, it has a thermal expansion coefficient which is equivalent to that of core ceramics) and can be fired at a temperature of not higher than a distortion point of a conventional ceramics core, so that when it is used as a porcelain, it can be fired without deforming the core and causing cracking and peeling. This makes it possible to suitably use the glass described above as a dental porcelain.

Among the glasses described above, the glass having a thermal expansion coefficient of $6.0 \times 10^{-6}$ (1/°C.) or less is hard to cause peeling and cracking when it is used as a dental porcelain for a core comprising, for example, the diopside base ceramics described above. The thermal expansion coefficient of glass varies depending on the composition thereof including those of optional components, and therefore it is difficult to specify indiscriminately the glass composition which provides the thermal expansion coefficient of $6.0 \times 10^{-6}$ (1/°C.) or less. However, the glass composition which provides the thermal expansion coefficient of $6.0 \times 10^{-6}$ (1/°C.) or less can be known by investigating in advance a relation of the compositions of various glasses falling in a range of the composition described above with the thermal expansion coefficient.

The dental porcelain of the present invention can be produced by pulverizing the glass obtained by the method described above to classify it to thereby obtain powder having a controlled particle size and adding, if necessary, a pigment, an oxidizing agent and the like.

The dental porcelain of the present invention is different in a suitable average particle diameter of the glass described above and the blending amount of a pigment depending on the use form thereof.

To be specific, when it is used as a body porcelain, an incisal porcelain or a cervical porcelain, the glass described above is preferably controlled in a particle size so that an average particle diameter of 15 to 100 $\mu$m can be obtained, and a pigment is preferably blended in an amount of 0.01 to 3 parts by weight per 100 parts by weight of the above glass.

Also, when it is used as a translucent porcelain, the glass described above is preferably controlled in a particle size so that an average particle diameter of 5 to 100 $\mu$m can be obtained, and a white pigment is preferably blended in an amount of 0.01 to 3 parts by weight per 100 parts by weight of the above glass.

When it is used as stain powders, the glass described above is preferably controlled in a particle size so that an average particle diameter of 1 to 15 $\mu$m can be obtained, and a pigment is preferably blended in an amount of 1 to 15 parts by weight per 100 parts by weight of the above glass.

Further, when it is used as glaze powders, the glass described above is preferably controlled in a particle size so that an average particle diameter of 1 to 15 $\mu$m can be obtained, and no specific additives are preferably added.

The pulverizing method shall not specifically be restricted, and publicly known pulverizing methods can be used. Examples of pulverizing equipments capable of being usually used include compression pulverizing equipments such as a jaw crusher and a cone crusher; ball mills such as a vibrating ball mill and an epicyclic mill; medium-stirring type crushers such as a tower type crusher, a stirring bath type crusher and an annular type crusher; high-speed rotary type impact crushers such as a pin mill and a disc mill; and other roll mills, a jet crusher and an autogenous crusher. Further, the classifying method shall not specifically be restricted, and publicly known classifying methods can be used. Examples of classifying equipments capable of being usually used include sieve classifiers such as a vibration sieve and a shifter; centrifugal classifiers such as a cyclone; and wet classifiers such as a settling classifier.

A pigment added to the dental porcelain of the present invention is added in order to color the porcelain after firing and control the translucence. In general, inorganic pigments are used as the above pigment since the porcelain is fired at a high temperature. Examples of typical pigments capable of being suitably used as the inorganic pigment include vanadium yellow, cobalt blue, chromium pink, iron chromium brown, zirconia white and titanium white.

An oxidizing agent is preferably added to the dental porcelain of the present invention in order to prevent organic matters contained as impurities from being introduced into the porcelain without being completely decomposed during firing to cause an inferior color tone of the porcelain. The above oxidizing agent shall not specifically be restricted as long as it is an oxygen-supplying source. Above all, suitably used is sulfate, particularly ammonium sulfate $(NH_4)_2SO_4$ which has a moderate oxidizing action and which sublimates essentially at a firing temperature or lower and does not remain in the fired article. The addition amount of the oxidizing agent shall not specifically be restricted and is usually 1 to 10 parts by weight per 100 parts by weight of the glass described above.

The dental porcelain of the present invention is piled on a ceramics core and then fired, whereby a dental porcelain crown composed of the core and the porcelain can be obtained. The core used in this case shall not specifically be restricted as long as it is a ceramics material, and glass ceramics such as mica, apatite, calcium phosphate and diopside can be used without limitation. Diopside base glass ceramics having a thermal expansion coefficient of 4 to $6\times10^{-6}$ (1/°C.) is suitably used from a viewpoint of a press moldability of a core material.

The piling method and firing method described above shall not specifically be restricted, and publicly known methods used for conventional porcelains can be used without limitation. For example, a powder of a porcelain is mixed with water, and the mixed matter is piled on a ceramic which is a core, followed by firing it.

In this case, use of a mixing liquid having a refractive index close to that of the porcelain instead of water is a preferred method from the viewpoint that mixed mud becomes semitransparent and an estimation of the color tone after firing is facilitated.

In piling, various porcelains are preferably piled in plural layers as shown in FIG. 1. Further, in order to reproduce a good color tone having a natural appearance, coloring is preferably provided using stain powders mixed with an organic solvent, or glaze powders mixed likewise with an organic solvent are preferably coated. Further, a body porcelain, an incisal porcelain, a cervical porcelain and a translucent porcelain are suitably fired at a firing temperature of 680 to 740° C., and stain powders and glazing powders are suitably fired at a firing temperature of 650 to 710° C. If fired at such high temperatures, the porcelains obtained after firing show a high chemical durability. For example, the acid dissolution amount is less than $100\,\mu g/cm^2$ in terms of a weight loss observed when the above porcelains are extracted in a 4% acetic acid aqueous solution for 16 hours according to ISO6872.

The physical properties of the porcelain obtained by firing the dental porcelain of the present invention such as a thermal expansion coefficient and the acid dissolution amount described above are almost the same as those of glass which is a principal component of the porcelain before firing.

The present invention shall specifically be explained below with reference to examples, but the present invention shall by no means be restricted by these examples. Methods for determining the firing temperatures in the examples and methods for evaluating the thermal expansion coefficients and the solubilities are as follows.

(1) Determining Method of Firing Temperature

Glass was pulverized in an alumina mortar and classified through a sieve of 200 mesh, and matters passing through the sieve were recovered to obtain a porcelain sample. This porcelain sample was mixed with water and filled into a mold having a thickness of 2 mm and a hole with a diameter of 10 mm while condensing to prepare a molded article. Seven molded articles were prepared by every glass composition, and the respective molded articles were fired respectively at different temperatures while changing the firing temperature by 10° C. in a range of plus and minus 30° C. centering on a temperature obtained by omitting the first place of the firing temperature expected from the composition thereof. Firing was carried out in a porcelain furnace Sigma 120 (manufactured by Tokuyama Co., Ltd.) which was an automatic electric furnace having a function capable of setting in advance a heating pattern on the conditions that a crucible charged with the molded article described above was maintained for 5 minutes under the furnace heated in advance at 500° C. to dry the article and then introduced into the furnace and that it was heated at a rate of 25° C./min. and maintained at a prescribed temperature for 2 minutes.

The fired article was observed, and a firing temperature at which the whole part was completely sintered to become semitransparent and irregularities formed by the porcelain particles were slightly observed without the surface being completely fused was recorded as the firing temperature of the porcelain sample.

(2) Evaluation Method of Thermal Expansion Coefficient

A rectangular parallelepiped of 2 mm×2 mm×10 mm was cut out from the glass to obtain a measurement sample, and the sample was heated from a room temperature to 500° C. by means of a thermal analytical equipment TMA120 (manufactured by Seiko Electron Co., Ltd.) to determine the thermal expansion coefficient.

(3) Evaluation Method of Acid Dissolution Amount

The acid dissolution amount was obtained by calculating the weight loss of the sample in terms of $\mu g/cm^2$ by a Soxhlet extraction method carried out in a 4% acetic acid aqueous solution for 16 hours according to International Standard (ISO 6872). The test piece was prepared by means of a mold having a diameter of 16 mm and a thickness of 1.6 mm.

EXAMPLE 1

Silicon dioxide (guaranteed reagent manufactured by Wako Pure Chemical Co., Ltd.) 30.4 g, aluminum oxide (guaranteed reagent manufactured by Kanto Chemical Co., Ltd.) 8.3 g, boron oxide (guaranteed reagent manufactured by Wako Pure Chemical Co., Ltd.) 8.7 g, lithium carbonate (guaranteed reagent manufactured by Wako Pure Chemical Co., Ltd.) 4.7 g, sodium carbonate (guaranteed reagent manufactured by Wako Pure Chemical Co., Ltd.) 4.0 g and zinc oxide (guaranteed reagent manufactured by Wako Pure Chemical Co., Ltd.) 1.1 g were mixed, and the mixture was molten at 1300° C. for 2 hours. Then, it was poured on a stainless steel plate and cooled to obtain homogeneous glass.

The composition of the glass and the measured firing temperature, thermal expansion coefficient and acid dissolution amount are shown in Table 1.

EXAMPLES 2 to 6

Glasses were prepared in raw material compositions shown in Table 1 according to the same method as in Example 1 to determine the firing temperatures, the thermal expansion coefficients and the acid dissolution amounts. As shown in Table 1, all the glasses of the present invention obtained in Examples 2 to 6 showed good results in all of firing temperatures, thermal expansion coefficients and acid dissolution amounts.

TABLE 1

| Example | SiO$_2$ | Al$_2$O$_3$ | B$_2$O$_3$ | Li$_2$O | Na$_2$O | ZnO | Firing temperature (° C.) | Thermal expansion coefficient × 10$^{-6}$ (/° C.) | Acid dissolution amount μg/cm$^2$ |
|---|---|---|---|---|---|---|---|---|---|
| 1 | 61 | 11 | 18 | 4 | 5 | 2 | 700 | 5.5 | 21 |
| 2 | 65 | 10 | 17 | 6 | 2.9 | 0.1 | 690 | 5.3 | 56 |
| 3 | 63 | 8 | 20 | 6 | 2 | 1 | 680 | 5.7 | 87 |
| 4 | 57 | 15 | 18 | 4 | 4 | 2 | 720 | 5.8 | 38 |
| 5 | 60 | 13 | 18 | 3 | 4 | 2 | 710 | 5.1 | 46 |
| 6 | 59 | 12 | 17 | 5 | 6 | 0.2 | 700 | 5.9 | 68 |

EXAMPLE 7

Diopside ceramics [distortion point: 724° C. and thermal expansion coefficient: 6.0×10$^{-6}$ (1/°C.)] was sintered in a casting mold to prepare a core for a front tooth crown. The casting mold used here was prepared by providing an abutment tooth model produced from gypsum with wax up, then setting a sprue wire to prepare a wax pattern and submerging the resulting wax pattern into a investment (gypsum), followed by hardening the investment and then burning the wax. Accordingly, the core prepared in the manner described above can be fitted to the abutment tooth model described above, and this fitting property has to be maintained even after firing various porcelains.

Next, the glass obtained in Example 1 was pulverized in an agate mortar to obtain powders having an average particle diameter of 37 μm, and the powders thus obtained were mixed with water. Then, the mixed matter was piled on the core prepared above and fired at a firing temperature of 700° C. As a result thereof, cracks on the porcelain surface and peeling between the porcelain and the core were not observed, and good firing was shown. Further, this fired article was set in the abutment tooth model made of gypsum which had been used when preparing the casting mold described above to investigate the fitting property, and it was found that the fitting property was good and deformation due to firing of the porcelain was not observed.

The glasses obtained in Examples 2 and 3 were subjected to the same test to find that cracks on the porcelain surface and peeling between the porcelain and the core were not observed, and good firing was shown. Further, the fitting property with the core after firing was good as well.

All the glasses obtained in Examples 4 to 6 described above show, as is the case with the glass of Example 1 used in Example 7 described above, lower firing temperatures than the distortion point of the diopside glass ceramics used as the core ceramics and as low thermal expansion coefficient as that of the above ceramics as well as a good chemical durability (low acid dissolution amount). Accordingly, they can suitably be used as a dental porcelain.

Comparative Example 1

A porcelain [Noritake Super Titan Body manufactured by Noritake Co., Ltd., thermal expansion coefficient: 7.8×10$^{-6}$ (1/°C.)] which was a commercial metal bond porcelain was used to carry out a firing test on a core in the same manner as in Example 7. The above porcelain is a powder of boron silicate glass. The firing temperature was set to 760° C. which was appointed by the maker. The porcelain was observed after firing to find that cracks were produced on the surface. Further, a slight distortion of the core was observed in the fitting property test on the gypsum model.

Comparative Examples 2 to 8

Glasses were prepared in raw material compositions shown in Table 2 according to the same method as in Example 1 to determine the firing temperatures, the thermal expansion coefficients and the acid dissolution amounts. The results are shown in Table 2.

TABLE 2

| Comparative Example | SiO$_2$ | Al$_2$O$_3$ | B$_2$O$_3$ | Li$_2$O | Na$_2$O | ZnO | Firing temperature (° C.) | Thermal expansion coefficient × 10$^{-6}$ (/° C.) | Acid dissolution amount μg/cm$^2$ |
|---|---|---|---|---|---|---|---|---|---|
| 2 | 56 | 18 | 15 | 6 | 3 | 2 | 750 | 5.5 | 201 |
| 3 | 66 | 8 | 19 | 3 | 3 | 1 | Not melt | — | — |
| 4 | 59 | 20 | 15 | 3 | 1 | 2 | 789 | 5.7 | 98 |
| 5 | 57 | 7 | 20 | 8 | 5 | 3 | 760 | 6.2 | 310 |
| 6 | 58 | 8 | 27 | 3 | 3 | 1 | 720 | 4.2 | 315 |
| 7 | 65 | 10 | 10 | 8 | 3 | 2 | 780 | 4.9 | 100 |
| 8 | 60 | 8 | 10 | 1 | 8 | 3 | 790 | 8.7 | 185 |

Comparative Example 2 is an example in which silicon oxide is decreased, wherein the acid dissolution amount grows large. Comparative Example 3 is an example in which the silicon oxide amount is increased, wherein melting was impossible, so that glass could not be produced. Comparative Example 4 is an example in which aluminum hydroxide is increased and sodium oxide is decreased, wherein the firing temperature is elevated. Comparative Example 5 is an example in which aluminum hydroxide is decreased and zinc oxide is increased, wherein the acid dissolution amount grows large. Comparative Example 6 is an example in which boron oxide is increased, wherein the acid dissolution amount grows large. Comparative Example 7 is an example in which boron oxide is decreased, wherein the firing temperature is elevated. Comparative Example 8 is an example in which boron oxide and lithium oxide are decreased and sodium oxide and zinc oxide are increased, wherein the firing temperature is elevated, and the thermal expansion coefficient and the acid dissolution amount grow large.

As shown in the examples described above, the dental porcelains of the present invention not only have a low thermal expansion coefficient and a good chemical durability but also are characterized by a low required firing temperature. Accordingly, the dental porcelain of the present invention do not bring about a deformation of the cores and the production of cracks after firing when used for the ceramics cores, and the aesthetic appearances can be maintained over a long period of time under an oral cavity environment.

What is claimed is:

1. A dental porcelain comprising glass containing silicon oxide, aluminum oxide, boron oxide, zinc oxide, sodium oxide and lithium oxide as principal components, wherein the contents of these respective components in the above glass are 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$ respectively in terms of a percent by weight based on the total of the respective components when the respective components are reduced to $SiO_2$, $Al_2O_3$, $B_2O_3$, ZnO, $Na_2O$ and $Li_2O$ respectively.

2. The dental porcelain as described in claim 1, wherein said dental porcelain is used for producing a crown using a ceramics core as a base.

3. The dental porcelain as described in claim 1 or 2, wherein the glass containing silicon oxide, aluminum oxide, boron oxide, zinc oxide, sodium oxide and lithium oxide as principal components has a thermal expansion coefficient of $6.0 \times 10^{-6}$ (1/°C.) or less.

4. The dental porcelain as described in claim 1 or 2, wherein said dental porcelain is a body porcelain.

5. The dental porcelain as described in claim 1 or 2, wherein said dental porcelain is a cervical porcelain.

6. The dental porcelain as described in claim 1 or 2, wherein said dental porcelain is an incisal porcelain.

7. The dental porcelain as described in claim 1 or 2, wherein said dental porcelain is a translucent porcelain.

8. The dental porcelain as described in claim 1 or 2, wherein said dental porcelain is stain powders.

9. The dental porcelain as described in claim 1 or 2, wherein said dental porcelain is glaze powders.

10. The dental porcelain as described in claim 3, wherein said dental porcelain is a body porcelain.

11. The dental porcelain as described in claim 3, wherein said dental porcelain is a cervical porcelain.

12. The dental porcelain as described in claim 3, wherein said dental porcelain is an incisal porcelain.

13. The dental porcelain as described in claim 3, wherein said dental porcelain is a translucent porcelain.

14. The dental porcelain as described in claim 3, wherein said dental porcelain is stain powders.

15. The dental porcelain as described in claim 3, wherein said dental porcelain is glaze powders.

16. Glass containing silicon oxide, aluminum oxide, boron oxide, zinc oxide, sodium oxide and lithium oxide as principal components, wherein the contents of these respective components are 57 to 65% by weight of $SiO_2$, 8 to 18% by weight of $Al_2O_3$, 15 to 25% by weight of $B_2O_3$, 0.1 to 2% by weight of ZnO, 3 to 7% by weight of $Na_2O$ and 2 to 8% by weight of $Li_2O$ respectively in terms of a percent by weight based on the total of the respective components when the respective components are reduced to $SiO_2$, $Al_2O_3$, $B_2O_3$, ZnO, $Na_2O$ and $Li_2O$ respectively; and the thermal expansion coefficient thereof is $6.0 \times 10^{-6}$ (1/°C.) or less.

* * * * *